US00PP13627P29

(12) United States Plant Patent
Vardi et al.

(10) Patent No.: US PP13,627 P2
(45) Date of Patent: Mar. 4, 2003

(54) CITRUS TREE NAMED 'YANOV'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Ramat-Gan (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,481

(22) Filed: Nov. 20, 2000

(51) Int. Cl.[7] ..... A01H 5/00
(52) U.S. Cl. ..... Plt./202

(58) Field of Search ..... Plt./202

(56) References Cited

PUBLICATIONS

GTITM UPOVROM Citation For 'Yanov' as per IL PBR02640; Feb. 26, 1999.*

* cited by examiner

*Primary Examiner*—Kent L. Bell
(74) *Attorney, Agent, or Firm*—Akerman Senterfitt

(57) ABSTRACT

A new variety of mandarin citrus is described that is distinguished by seedless fruit having a ripening period from mid-November to December in Israel and very low pollen fertility.

2 Drawing Sheets

FIELD OF THE INVENTION

A new mandarin citrus tree hybrid *Citrus reticulata* is described. The new variety named 'Yanov' is desirable because of its lack of seeds and early ripening period between mid-November to December.

BACKGROUND OF THE NEW PLANT

The present invention relates to a new and distinct variety of mandarin citrus tree Citrus reticulata hybrid developed by inventors Aliza Vardi, Pinchas Spiegel-Roy, Avraham Elchanati, Ahuva Frydman-Shani and Hana Neumann in Bet Dagan, Israel from a selection of plants grown from irradiated bud wood of the cultivar Nova.

Asexual reproduction by conventional bud grafting of the new variety at the Agriculture Research Organization Volcani Center in Bet Dagan, Israel, has shown that the new characteristics are stabilized and permanently fixed through successive propagation.

The objective in breeding the present new tree variety, known by the cultivar name 'Yanov', was to obtain a mid season ripening variety with few or no seeds. In the spring of 1987 and 1988 about 200 buds of the mandarin cultivar 'Nova' (unpatented) were irradiated at the Nahal Soreq Nuclear Center, Yavne, Israel, by exposure to 3.5 kh of gamma radiation from a Co60 source. Sour orange nucellar rootstocks were bud grafted with the individual buds of irradiated Nova bud wood and labeled $mV_1$. Six to nine months after grafting the irradiated budwood, individual buds from the $mV_1$ plants were re-grafted on Sour orange nucellar rootstocks to establish about 350 $mV_2$ plants.

Field planting was established from container grown $mV_2$ plants in the spring of 1989 and 1990. The first fruits were observed in January–March 1992 and a second observation made January–March of 1993 and 1994.

SUMMARY OF THE INVENTION

One of the selections, designated 1/22/20, had medium sized orange color fruit and was relatively easy to peel. The selection was distinguished from 'Nova' as having seedless fruit compared with 9–25 seeds for 'Nova' and having mainly sterile pollen. Typically 2% of the pollen grains of the selection were stained by acetocarmine compared with 95% for 'Nova'.

Color designations have been determined from The R.H.S. Colour Chart published by The Royal Horticultural Society, London.

Table 1 shows some of the characteristics of the new tree compared to the parent 'Nova'.

TABLE 1

| Tree | Fruit skin color | Peelability | Seeds/fruit | Pollen fertility[1] |
|---|---|---|---|---|
| 1/22/20 'Yanov' | RHS 25A | Easy | 0 | 2% |
| 'Nova' | RHS 25A | Easy | 9–27 | 95% |

[1]Estimated by Acetocarmine staining

The following is a detailed description of the new mandarin citrus variety based on observations made under typical Israli grove conditions.

The tree shape and fruit appearance is similar to that of 'Nova'. The tree has medium vigor. Very few thorns usually are present in the leafy part of branches, especially in the lower portion. Main branches have an upright attitude and young shoots have no anthocyanin coloration at the tip. The bearing of the tree is regular and the productivity is relatively high, about the same as for 'Nova'. The canopy is moderately dense.

The leaves are similar to those of 'Nova'. The leaf blade length is short to medium and the width is narrow to medium, the cross section is concave, the firmness is weak and the color is green. The petiole is narrow and very short to short.

The characteristics of the flowering and the flower parts are similar to those of 'Nova'. Flowering for both occurs in end of March or in first half of April as measured in Bet Dagan, Israel. Both 'Yanov' and 'Nova' produce about the same number of flowers and flower drop for both occurs in April. Terminal flower buds have no anthocyanin coloration. Flowers are borne singly and have an average number of stamens (about 20) with complete style development. Anther color is pale yellow to white. Pollen fertility is very low as indicated by the observation that only 2% of the pollen grains were stained with acetocarmine in a test conducted at the Agricultural Research Organization, the Volcani Center, Israel, as compared with stainability of about 95% for Nova pollen grain.

All the flowers of mandarin cultivars are very much alike in color of petal (both sides are white), anther, pistil, etc.

The fruit is seedless even when optimal pollination conditions are employed. This compares with about 9–27 seeds per fruit in 'Nova' when optimal pollination conditions are employed. In other respects the fruit characteristics are in the range of the parent cv. 'Nova'. The fruit shape is oblate and medium sized. When 50 fruits were measured, the fruit had an average weight 120 grams, an average height 58 mm, and an average diameter 65 mm. The fruit has a moderately depressed stalk end. The fruit surface is usually smooth with a yellow-orange color, 25A, on The Royal Horticultural Society of London Colour Chart, and bears an average number of conspicuous rind oil glands. Fruit ripening does not differ from outside of the canopy to the inside, but the fruit color of the outside canopy is a little brighter compared to the fruit color of the inside canopy. There is no persistence of the style and the areola is not completely developed. A navel is typically absent but sometimes present. The rind is thin and easy to peel.

The color of the albedo is white and the flesh is orange in color. The fruit contains 11–13 segments and is juicy. The external color of the seeds (when fresh) and dry is white. The internal seed coat is pale brown and the cotyledons are green. Polyembryonic seeds are present. The seed sizes, shape and texture are similar to that of the parent 'Nova'mandarin. The fruit reaches maturity in mid-November to the end of December. The ripening of the fruit on the tree and within the fruit is uniform. If there is a heavy crop and the fruits are not picked before end of December it may becomes an alternate bearing (produces less fruit the following season). Pre-harvest drop of both developed and underdeveloped fruit is similar to that of the parent 'Nova' mandarin.

DESCRIPTION OF THE PHOTOGRAPHS

The new citrus tree is illustrated in the accompanying color photographs.

Sheet one depicts the whole tree and canopy shape of the new variety.

Sheet two shows the exterior of the fruit as well as transverse midsections in a plane substantially perpendicular to the axis, illustrating no seeds in the interior of the fruit.

DESCRIPTION OF THE NEW TREE

The following is a detailed description of the new mandarin citrus variety 'Yanov' based on observations made under typical Israeli grove conditions. Observations were made on trees approximately 4–5 years old.

Tree:

*Origin.*—Irradiation of cv. 'Nova'.

*Classification.*—Botanical: *Citrus reticulata* hybrid. Common: Mandarin citrus. Cultivar: 'Yanov'.

*Shape.*—Somewhat round-topped.

*Thorns.*—Fruit bearing buds are thornless.

*Branching.*—Upright.

*Canopy.*—Moderately dense.

*Bark.*—Immature: Green RHS 137B. Mature: Greyed-green RHS 189A.

*Leaf.*—Color: Upper: green RHS 146A; lower: green RHS 146B. Size: Lanceolate taper-pointed, 76 mm length, 22 mm width. Leaf blade: concave cross section. Petioles: Short and wingless: 8 mm in length, 2 mm in diameter, Green RHS 146. Firmness: Weak.

*Habit.*—Moderately vigorous.

*Height.*—2–2.5 m.

*Disease resistance.*—No particular susceptibility or resistance observed.

*Trunk diameter.*—8 cm at 20 cm above the ground.

*Tree spread diameter.*—Dependent on distance within row and pruning.

*Winter hardiness.*—Winter temperature in Bet Dagan, Israel averages 4–7 degrees Centigrade.

Flower:

*Flowering period.*—Late March–early April in Israel.

*Petals.*—5.

*Petal color.*—Upper and lower: RHS 155D.

*Flower drop.*—April.

*Stamens.*—Approximately 20.

*Anther color.*—Yellow RHS 11C.

*Pollen fertility.*—Low, 2% by acetocarmine staining.

*Anthocyanin coloration.*—No coloration.

Fruit:

*Productivity.*—80 kg/tree per season. *Shape.*—Oblate. *Size.*—Medium. *Weight.*—120 g (average of 50 fruits). *Height.*—58 mm. *Diameter.*—65 mm.

*Skin color.*—Orange RHS 25A.

*Rind oil gland.*—Conspicuous (35 $cm^2$).

*Style.*—No persistence.

*Navel.*—Absent.

*Rind.*—Thin (2–3 mm) and easy to peel.

*Albedo.*—Yellow-orange RHS 18C.

*Areola.*—Incompletely developed.

*Fruit segments.*—11–13.

*Color of flesh.*—Orange RHS 25A.

*Time to maturity.*—Mid November–December.

*Fruit extract.*—(Test conducted on Dec. 16, 1997 on juice of representative fruit). Total soluble solids (TSS) 13.2%. Acid content: 1.1%. TSS/acid ratio 12. Flavor: Pleasant.

Seeds: No seeds.

The tree and its fruit as described herein may vary somewhat in certain characteristics due to climatic and/or soil conditions under which the variety is grown. All the observations were made at Bet-Dagan, The Volcani Center, Israel on 4–5 year old trees.

What is claimed is:

1. A new and distinct variety of *Citrus reticulata* hybrid tree substantially as herein described and shown.

* * * * *

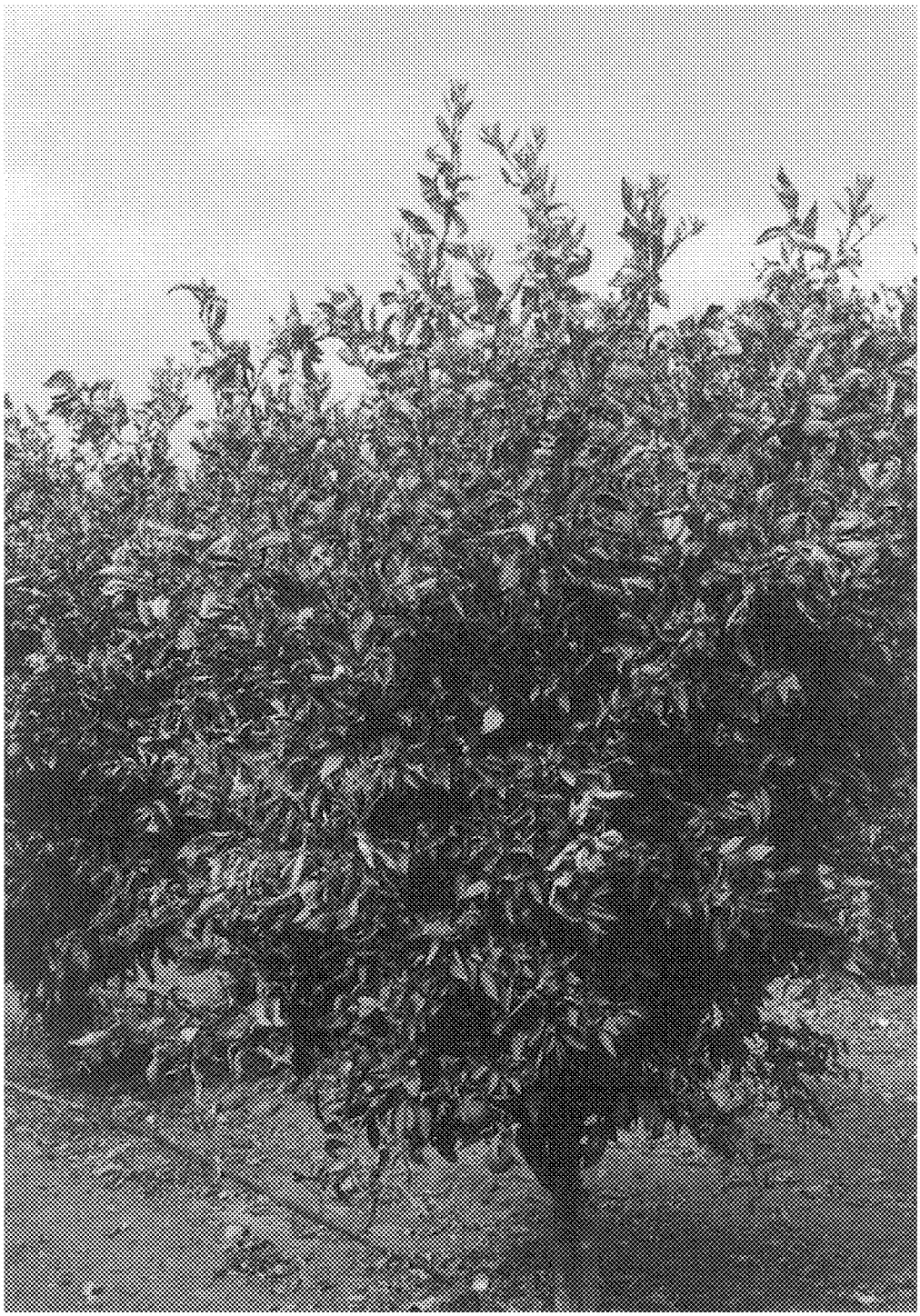

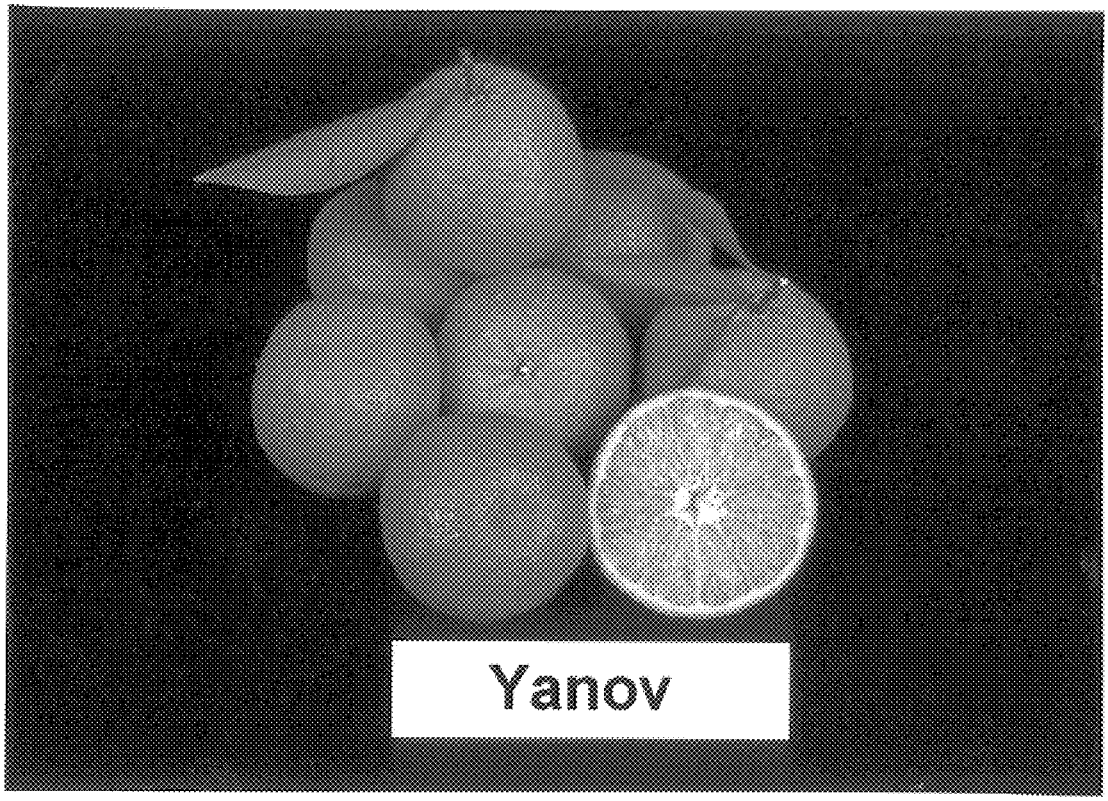
Yanov